(12) United States Patent
Hermony

(10) Patent No.: US 9,173,618 B2
(45) Date of Patent: Nov. 3, 2015

(54) DIAGNOSTIC IMAGING SYSTEM AND METHOD USING MULTIPLE TYPES OF IMAGING DETECTORS

(75) Inventor: Nathan Hermony, Ceasarea (IL)

(73) Assignee: General Electric Company, Schenectady, NY (US)

( * ) Notice: Subject to any disclaimer, the term of this patent is extended or adjusted under 35 U.S.C. 154(b) by 834 days.

(21) Appl. No.: 12/613,368

(22) Filed: Nov. 5, 2009

(65) Prior Publication Data

US 2011/0103544 A1    May 5, 2011

(51) Int. Cl.
| | |
|---|---|
| G01T 1/166 | (2006.01) |
| A61B 6/03 | (2006.01) |
| G01T 1/161 | (2006.01) |
| G01T 1/29 | (2006.01) |
| A61B 6/00 | (2006.01) |
| G01T 1/16 | (2006.01) |

(52) U.S. Cl.
CPC .............. *A61B 6/032* (2013.01); *A61B 6/037* (2013.01); *A61B 6/5235* (2013.01); *G01T 1/1611* (2013.01); *G01T 1/2985* (2013.01); *A61B 6/4266* (2013.01); *A61B 6/4417* (2013.01); *A61B 6/4429* (2013.01); *A61B 6/503* (2013.01); *G01T 1/1603* (2013.01)

(58) Field of Classification Search
USPC .................................................... 250/363.05
See application file for complete search history.

(56) References Cited

U.S. PATENT DOCUMENTS

| | | | | |
|---|---|---|---|---|
| 4,785,186 | A * | 11/1988 | Street et al. | 250/370.14 |
| 5,354,993 | A | 10/1994 | Kedmi et al. | |
| 5,585,638 | A * | 12/1996 | Hoffman | 250/370.07 |
| 6,583,420 | B1 * | 6/2003 | Nelson et al. | 250/397 |
| 6,670,614 | B1 * | 12/2003 | Plut et al. | 250/363.04 |
| 6,728,583 | B2 | 4/2004 | Hallett | |
| 7,012,257 | B2 | 3/2006 | Juni | |
| 7,015,476 | B2 | 3/2006 | Juni | |
| 7,071,473 | B2 | 7/2006 | Juni | |
| 7,105,825 | B2 | 9/2006 | Juni | |
| 7,573,039 | B2 | 8/2009 | Smith | |
| 7,592,597 | B2 | 9/2009 | Hefetz et al. | |
| 7,593,502 | B2 | 9/2009 | Katcha et al. | |
| 2002/0090050 | A1 * | 7/2002 | Nutt et al. | 378/19 |
| 2002/0143249 | A1 * | 10/2002 | Tornai et al. | 600/425 |
| 2005/0194540 | A1 * | 9/2005 | Fenster et al. | 250/363.05 |
| 2010/0171041 | A1 * | 7/2010 | Iida | 250/394 |

FOREIGN PATENT DOCUMENTS

WO    WO 2007013550 A1 *    2/2007

* cited by examiner

*Primary Examiner* — David Porta
*Assistant Examiner* — Shun Lee
(74) *Attorney, Agent, or Firm* — Dean D. Small; The Small Patent Law Group, LLC

(57) ABSTRACT

A diagnostic imaging system and method using multiple types of imaging detectors are provided. The imaging system includes a gantry having a rotor and a stator and a pair of gamma detectors coupled to the rotor. The imaging system further includes a gamma detector coupled to the stator. The gamma detector coupled to the stator is different than the pair of gamma detectors coupled to the rotor.

13 Claims, 8 Drawing Sheets

DIAGNOSTIC IMAGING SYSTEM AND METHOD USING MULTIPLE TYPES OF IMAGING DETECTORS

BACKGROUND OF THE INVENTION

This subject matter disclosed herein relates generally to diagnostic imaging systems, and more particularly to Nuclear Medicine (NM) imaging systems with multiple detectors on a gantry.

In NM imaging, radiopharmaceuticals are taken internally and then detectors (e.g., gamma cameras), typically mounted on a gantry, capture and form images from the radiation emitted by the radiopharmaceuticals. The NM images primarily show physiological function of, for example, a patient or a portion of a patient being imaged.

In some types of scans, such as when scanning the whole body or with large patients, the portion of the patient being imaged may require the entire field of view of a conventional large size imaging detector. However, when imaging a structure that is smaller than the field of view of the imaging detector, such as the heart, liver, kidney, brain, breast or a tumor, portions of the imaging detector will acquire patient data outside of the structure of interest. Therefore, an effective sensitivity is decreased that is unrelated to collimator geometrical sensitivity, but results from the opportunity lost by not collecting useful information.

Many types of scans also require imaging from a number of axial positions around the patient. For example, conventional imaging detectors often acquire data while being rotated by a gantry around at least a portion of the patient, such as 180 degrees and up to 360 degrees, to obtain sufficient data of the structure for volumetric imaging and processing. This is a time consuming imaging process, particularly for organ specific imaging, which thereby limits patient throughput.

BRIEF DESCRIPTION OF THE INVENTION

In accordance with an embodiment, an imaging system is provided that includes a gantry having a rotor and a stator and a pair of gamma detectors coupled to the rotor. The imaging system further includes a gamma detector coupled to the stator. The gamma detector coupled to the stator is different than the pair of gamma detectors coupled to the rotor.

In accordance with another embodiment, an imaging system is provided that includes a gantry, a first general purpose gamma detector coupled to the gantry and a second general purpose gamma detector coupled to the gantry opposite the first general purpose gamma detector. The imaging system further includes an organ specific gamma detector coupled to the gantry.

In accordance with yet another embodiment, a method of providing a nuclear medicine imaging system includes coupling a first type of gamma detector to a gantry and coupling a second type of gamma detector to the gantry. The method further includes configuring the first type of gamma detector to rotate about the gantry and move inward and outward from an examination axis using a gantry that provides motion along a single axis. The method also includes configuring the second type of gamma detector to move toward and away from the gantry.

DETAILED DESCRIPTION OF THE INVENTION

Figure 1:
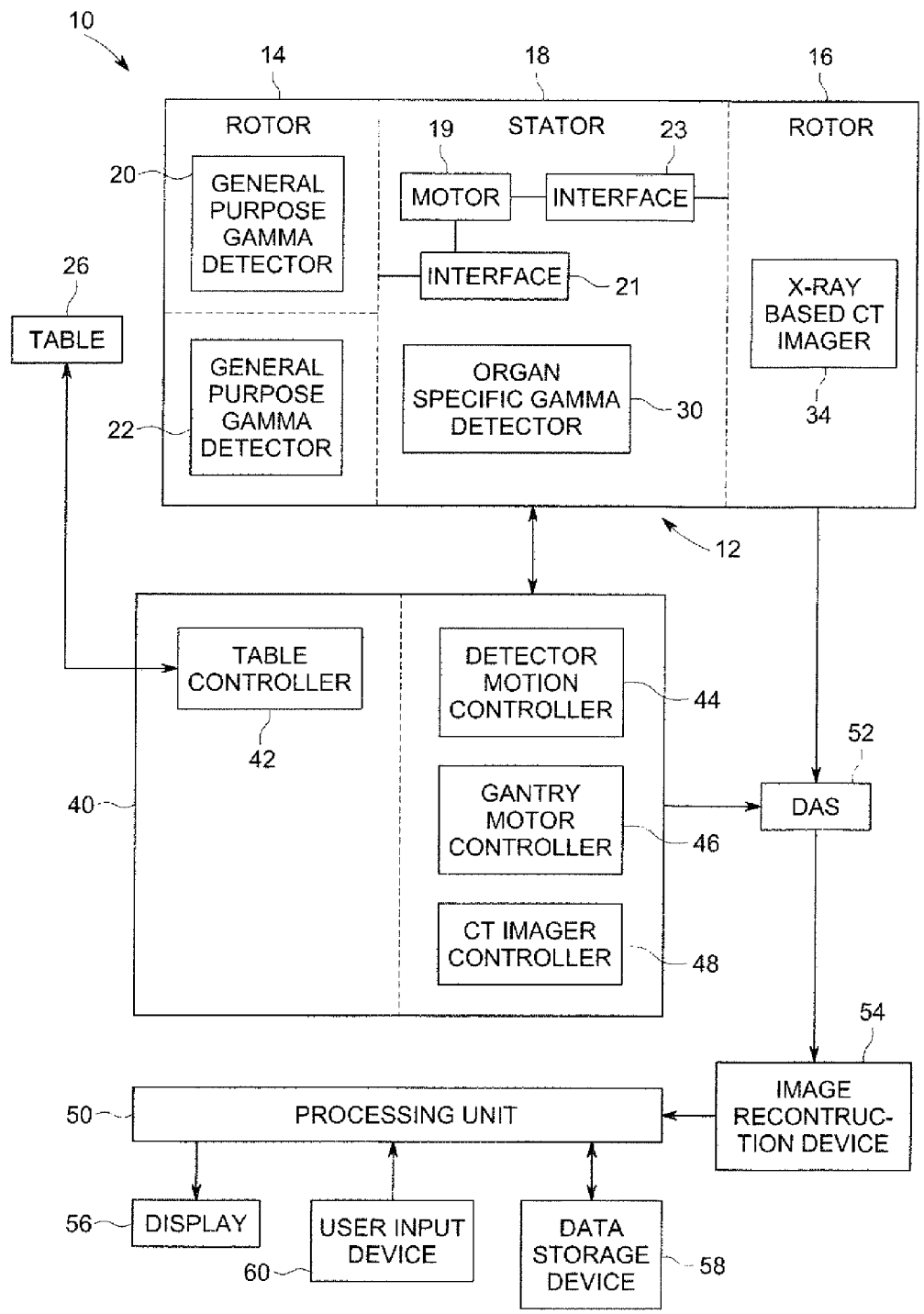
FIG. 1 is a block diagram of an imaging system formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a diagnostic imaging system, such as a Nuclear Medicine (NM) imaging system having a gantry with a plurality of different types of imaging detectors mounted thereto. For example, in various embodiments of an NM imaging system, one or more general purpose (GP) gamma camera detectors and at least one smaller region or organ specific gamma camera detector are provided in connection with the gantry.

Figure 2:
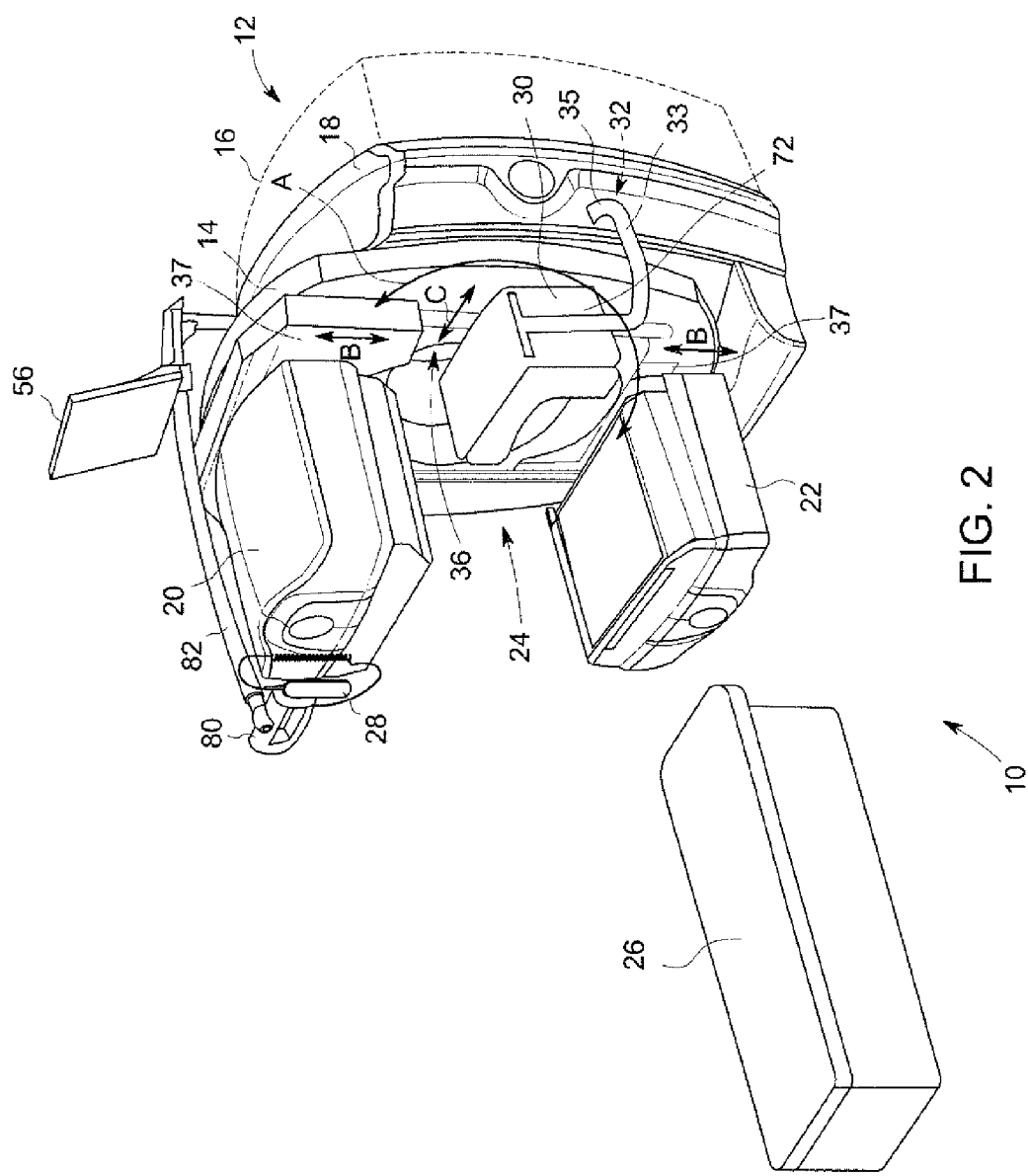
FIG. 2 is a perspective view of the imaging system of FIG. 1.

Specifically, with reference to FIGS. 1 and 2, a NM imaging system 10 having a gantry 12 formed in accordance with various embodiments is illustrated. The gantry 12 generally includes a stator rotor arrangement having a first rotor 14, an optional second rotor 16 (illustrated in FIG. 2 as a separate gantry unit) and a stator 18. In some embodiments, the first rotor 14 and second rotor 16 are separated by the stator 18 as illustrated. For example, the first rotor 14 may be provided on a front of the stator 18 and the second rotor 16 may be provided on a back of the stator 18. It should be noted that the first and second rotors 14 and 16 may be coupled to the stator 18 in any suitable manner, for example, mounted thereto to provide rotational movement about an examination axis. It also should be noted that the first and second rotors 14 and 16 may optionally be mounted adjacent each other such that the stator 18 is not provided therebetween.

In the various embodiments, at least one of the first and second rotors 14 and 16 are connected to a motor 19 of the stator 18 via an interface 21 and 23, respectively. For example, a ball bearing (not shown) is provided between the stator 18 and the first rotor 14 and/or the second rotor 16. In various embodiments, the interface 21 may be a tooth wheel and the interface 23 may be a belt. Accordingly, tooth wheel driven or belt drive operation may be provided. Thus, in operation, the motor 19 rotates one of the first and/or second rotors 14 and 16 via the interface 21 and interface 23, respectively. It should be noted that a separate motor may be provided for rotating each of the first and second rotors 14 and 16 and configured, for example, as separate gantries. Thus, in operation the one more gamma detectors rotate around an examination axis 24 of the gantry 12. In the various embodiments, the first and second rotors 14 and 16 are non-stationary portions, capable or movement (e.g., rotation) and the stator 18 is a stationary or static portion. In some embodiments, a retractor (not shown) is provided between the first rotor 14 and the stator 18 and a slip ring (not shown) is provided between the second rotor 16 (and optionally the first rotor 14 instead of the retractor) and the stator 18.

The gantry 12 generally includes a first type of gamma detector, for example, a first general purpose gamma camera 20 and a second general purpose gamma camera 22 (both configured in the illustrated embodiment as gamma cameras) coupled to the first rotor 14. The first and second general purpose gamma cameras 20 and 22 are mounted to the first rotor 14 to detect gamma rays emitted from a radiopharmaceutical within a patient (not shown). In the illustrated embodiments, the second general purpose gamma camera 22 is mounted on the first rotor 14 opposite the first general purpose gamma camera 20 such that the first and second general purpose gamma cameras 20 and 22 are arranged in an H-mode. The first and second general purpose gamma cameras 20 and 22 are provided such that the gantry 12, and particularly the first rotor 14 rotates the first and second general purpose gamma cameras 20 and 22 (illustrated by the arrow A) about the examination axis 24 (around a patient) supported on a patient table 26 to detect coincident emissions of gammas, for example, for use in Positron Emission Tomography (PET) or in Single Photon Emission Computed Tomography (SPECT) imaging. It should be noted that the rotation of the first rotor 14 may be controlled from a connected console (as is known), using a connected handheld controller 28 as shown in FIG. 2 or optionally remotely.

The first and second general purpose gamma cameras 20 and 22 may be formed in any know manner for use in scanning larger areas, for example, a full body scan of a patient. The first and second general purpose gamma cameras 20 and 22 may be formed from Sodium Iodide (NaI) detector elements and used in combination with photomultiplier (PMT) tubes as is known.

A second type of gamma detector, for example, an organ specific gamma detector 30 is also coupled to the gantry 12, and more particularly to the stator 18. For example, the organ specific gamma detector 30 may be mounted to a side of the stator 18 using a mounting structure 32 such as a mounting bracket or other support member. The mounting structure includes a support arm 33 to support and position the organ specific gamma detector 30. In various embodiments, the mounting structure 32 optionally provides pivoting or swiveling movement at a pivot point 35 such that the organ specific gamma detector 30 may be moved toward and away from the gantry 12, for example, sideways from the gantry 12. Additionally, the support arm 33 may be configured to provide horizontal movement of the organ specific gamma detector 30 towards and away from the examination axis 24 as illustrated by the arrow C. The support arm 33 may be extendible or retractable to provide the horizontal movement. In some embodiments, only horizontal movement is provided (e.g., using the extending support arm 33) and vertical alignment of the organ specific gamma detector 30 with the patient is provided by vertical movement of the patient table 26.

Accordingly, the organ specific gamma detector 30 may be movable using a pivoting or swinging motion such that the organ specific gamma detector 30 may swing toward and away from the gantry 12 and a horizontal movement to move the organ specific gamma detector 30 toward and away from the examination axis 24. The pivoting or swinging movement allows the organ specific gamma detector 30 to be moved such that rotation of the first and second general purpose gamma cameras 20 and 22 on the rotor 14 of the gantry 12 about the examination axis 24 is provided. The horizontal movement allows for closer positioning of the organ specific gamma detector 30 to a patient supported on the patient table 26.

Optionally, an x-ray based Computed Tomography (CT) imager 34 is coupled to the second rotor 16. In some embodiments, the CT imager 34 includes a separate gantry to form a dual-modality imaging system. The CT imager 34 may be any type of CT imaging device as is known and that operates to provide, for example, attenuation correction and anatomical registration information (as well as image information). The attenuation correction and anatomical registration may be provided using any known methods. In operation, the patient table 26 may extend further along the examination axis 24 such that a patient is moved through a bore 36 of the gantry 12 to a field-of view (FOV) of the CT imager 34 on the back side of the gantry 12, namely coupled to the second rotor 16. The movement of the CT imager 34, and in particular rotational movement about the patient, is similar to that of the first and second general purpose gamma cameras 20 and 22. However, the CT imager 34 includes an x-ray source and an x-ray detector mounted opposite each other on the second rotor 16.

A controller unit 40 controls the movement and operation of the various components of the NM imaging system 10. In particular, the controller unit 40 controls the movement and/or operation of the first and second general purpose gamma cameras 20 and 22, patient table 26, the organ specific gamma detector 30 and optionally the CT imager 34. It should be noted that the movement of these components may be controlled electronically using motors connected to the components. However, in some embodiments, some of the components may not be moved using motors, but instead manually positioned by an operator. For example, the organ specific gamma detector 30 may be manually positioned using the mounting structure 32 and support arm 33.

The controller unit 40 generally includes a table controller 42, a detector motion controller 44, a gantry motor controller 46 and a CT imager controller 48. The table controller 42 (which may form part of or be commanded by the handheld controller 28) controls movement of the patient table 26 to position the patient relative to the FOV of the first and second general purpose gamma cameras 20 and 22, the organ specific gamma detector 30 and/or optionally the CT imager 34. The patient table 26 may be moved, for example, in an up-down direction, in-out direction (e.g., advancing the patient along the examination axis 24) and right-left direction. The detector motion controller 44 controls the position of the first and second general purpose gamma cameras 20 and 22, and in particular, moves the first and second general purpose gamma cameras 20 and 22 radially inward and outward motion toward and away from a patient in the embodiment illustrated in FIGS. 1 and 2 using brackets 37. The brackets 37 allow translational or sliding movement of the first and second general purpose gamma cameras 20 and 22 along a single axis, for example, radially inward and/or outward (e.g., transverse to the examination axis 24) when the first and second general purpose gamma cameras 20 and 22 are at a particular angularly rotated position. Thus, the bracket 37 movably couples the first and second general purpose gamma cameras 20 and 22 to the rotor 14. It should be noted that in various embodiments, the brackets 37 allow movement only along the single axis, namely back and forth in the same direction.

The gantry motor controller 46 controls the positioning of the first and second general purpose gamma cameras 20 and 22 about the patient, for example, controls the rotation, rotational position and rotational speed of the first and second general purpose gamma cameras 20 and 22 using the first rotor 14. The CT imager controller 48 controls the movement of as well as provides power and timing signals to the CT imager 34.

Thus, in operation, in addition to rotational movement of the first and second general purpose gamma cameras 20 and 22 about the patient, the first and second general purpose gamma cameras 20 and 22 in various embodiments may be moved radially in and out, namely closer or farther away from a patient with respect to the examination axis 24 as illustrated by the arrows B (in FIG. 2). The inward and outward movement of the first and second general purpose gamma cameras 20 and 22 closer to and further away from a surface of the patient may be provided, for example, as a translating movement using the brackets 37. In some embodiments, this inward and outward movement is the only motion provided. For example, no swivel or other motion is provided to the first and second general purpose gamma cameras 20 and 22.

The controller unit 40 may be automatically commanded by a processing unit 50, manually controller by an operator (e.g., using the handheld controller 28), or a combination thereof. It should be noted that the first and second general purpose gamma cameras 20 and 22 (or the organ specific gamma detector 30) and patient table 26 in some embodiments remain stationary after being initially positioned, and imaging data is acquired and processed as discussed below. The imaging data may be combined and reconstructed into a composite image, which may comprise 2D images, a 3D volume or a 3D volume over time (4D). In other embodiments, the first and second general purpose gamma cameras 20 and 22 rotate to acquire image data.

A data acquisition system (DAS) 52 receives electrical signal data produced by the first and second general purpose gamma cameras 20 and 22, the organ specific gamma detector 30 (and optionally the detector of the CT imager 34) and converts the data into digital signals for subsequent processing. An image reconstruction device 54 receives data from the DAS 52 to reconstruct an image from the received data to generate an image for display on a display 56. A data storage device 58 also may be provided for storing data, which may be stored either short term (e.g., during processing) or long term for later retrieval. A user input device 60 (e.g., keyboard, mouse, trackball, etc.) may be provided to receive user input for controlling the NM imaging system 10. It should be noted that the user input device 60 may form part or be embodied as the handheld controller 28.

It also should be noted that one or more functions related to one or more of data acquisition, motion control, data processing and image reconstruction may be accomplished through software and by shared processing resources, which may be located within or near the NM imaging system 10, or may be located remotely.

The NM and optional CT functions may be used together or separate from each other. The gantry 12, and in particular, the first and second rotors 14 and 16, in combination with the patient table 26 may be controlled to provide co-registration of image data acquired using the NM and CT functions. For example, the system position may be defined by the processing unit 50 to identify the positions of all components and a relation to each other with respect to a predetermined reference point. The components may be any fixed or moving structure, such as the patient table 26, the first and second general purpose gamma cameras 20 and 22, the organ specific gamma detector 30 and/or optionally the x-ray source and detector of the CT imager 34, and the like, each of which references the predetermined reference point, such as a zero position or an initial reference position.

In some embodiments, the first and second general purpose gamma cameras 20 and 22 may be operated in a persistence mode. The table controller 42 moves the patient table 26 while the DAS 52 and/or processing unit 50 detect a count rate from each of the first and second general purpose gamma cameras 20 and 22. For example, the patient may be positioned on the patient table 26 to be equidistant between the first and second general purpose gamma cameras 20 and 22. The table controller 42 may first move the patient table 26 along the in-out direction along the examination axis 24 to determine a horizontal table position having a maximum count rate. The table controller 42 may then move the patient table 26 along the up-down direction to determine a vertical table position having a maximum count rate.

In the NM imaging system 10, the first and second general purpose gamma cameras 20 and 22 are generally larger size or dimensioned gamma ray detectors than the organ specific gamma detector 30, which is configured for imaging a smaller region, such as a heart, lungs, brain, etc. of a patient. The first and second general purpose gamma cameras 20 and 22 may be formed from NaI, such that each is formed from a single NaI crystal and includes a plurality of photomultiplier tubes (PMTs) as is known. For example, the first and second general purpose gamma cameras 20 and 22 may each have dimensions of approximately 50 cm by 40 cm and include sixty or more PMTs in combination therewith. The first and second general purpose gamma cameras 20 and 22 in the various embodiments are configured for general purpose NM imaging, which typically includes imaging larger regions, such as a portion of patient or the whole patient.

The first and second general purpose gamma cameras 20 and 22 may be fixed in angular orientation with respect to each. In particular, the first and second general purpose gamma cameras 20 and 22 are positioned opposite each other on the first rotor 14, namely 180 degree apart facing each other in various embodiments. Accordingly, the first and second general purpose gamma cameras 20 and 22 are maintained in an H-mode configuration. In these embodiments, the first and second general purpose gamma cameras 20 and 22 are not adjustable to be positioned in an L-mode configuration, for example, for cardiac imaging, which is performed using the organ specific gamma detector 30. Accordingly, the first rotor 14 in various embodiments allows for movement of each of the first and second general purpose gamma cameras 20 and 22 around the patient and radially inward and outward (as illustrated by the B arrows in FIG. 2), but not titled or moved to different positions along the gantry circumference. The first and second general purpose gamma cameras 20 and 22 may be formed and provided similar to the gamma cameras in the Infinia and Millennium imaging systems available from GE Healthcare.

Figure 3:
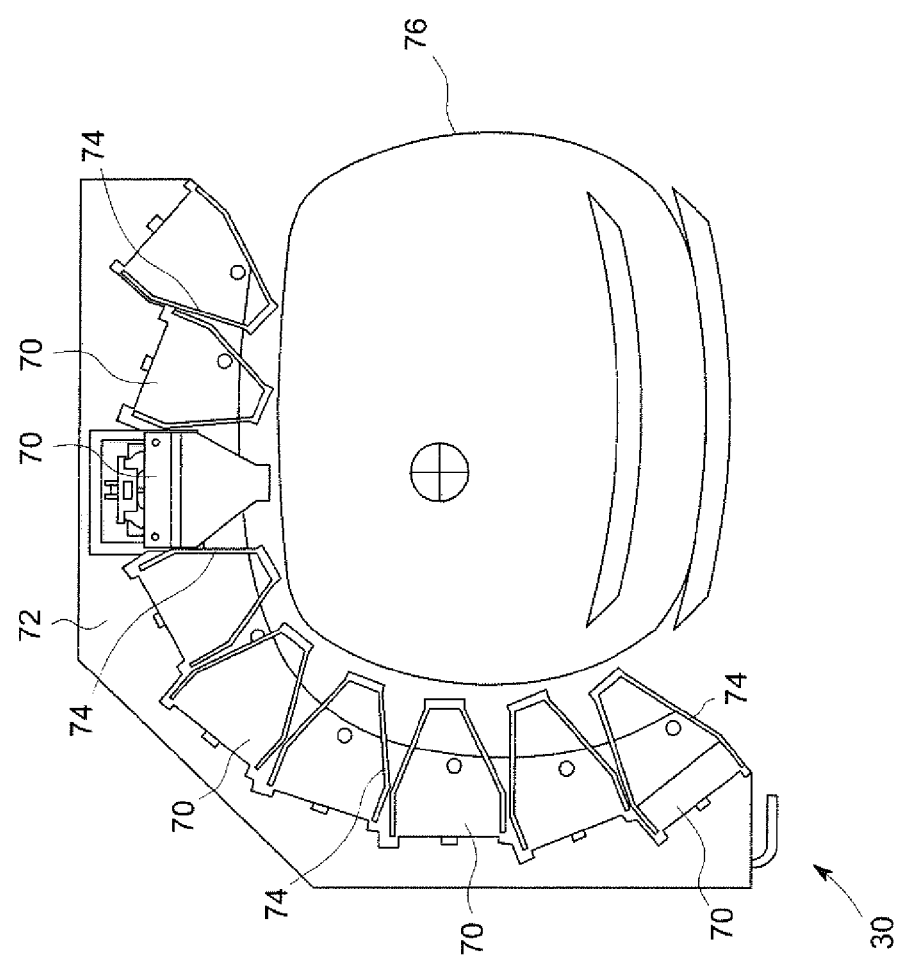
FIG. 3 is a diagram illustrating an organ specific gamma camera of the imaging system of FIG. 1.

In the various embodiments, especially as illustrated in FIGS. 1 and 2, the organ specific gamma detector 30 has a multi-gamma camera, multi-pinhole detector arrangement, which for example, as shown in FIG. 3, is arranged in an L-shaped configuration similar to an L-mode of operation. The organ specific gamma detector 30 includes a plurality of solid-state two-dimensional (2D) detector arrays 70, for example, a plurality of Cadmium Zinc Telluride (CZT) detector arrays. Each of the detector arrays 70 is configured as an independent gamma camera having a fixed orientation. In particular, each of the detector arrays 70 is fixed on a support structure 72, which is in an L-shape or semi-arc shape, such that the detector arrays 70 conform to the shape of a patient. Each of the detector arrays 70 includes a corresponding pinhole collimator 74 such that the detector arrays 70 are focused gamma cameras for imaging a smaller region, such as an organ of the patient (e.g., heart, lung, brain, etc.). In the illustrated embodiment, the detector arrays 70 with the pinhole collimators 74 are focused to image a heart region (shown as the imaged region) within the patient 76. The illustration shows the imaged region as would as be displayed on the display 56 (shown in FIGS. 1 and 2), which is typically a persistent mode display showing a current image being acquired by the organ specific gamma detector 30.

The detector arrays 70 are positioned and oriented, for example, angled to focus on a particular area. For example, for cardiac imaging, the detector arrays 70 are positioned and oriented to focus on a location including a heart of a patient. Thus, each of the detector arrays 70 may be angled differently to focus on the area of interest. It should be noted that in some embodiments, multiple rows of detector arrays 70 are provided. For example, three rows of nine detector arrays 70 (only one row is shown in FIG. 3) may be provided. In this triplet configuration, each set of three detector arrays 70 is mounted to a motherboard and defines a plane of the solid-state detector triplet. It should be noted that the detector arrays 70 in each triplet may be angled differently, for example, the outer two detector arrays 70 (e.g., on the ends of each triplet) may be angled more inward to focus on the area of interest. Each of the triplets of detector arrays 70 may be separated (e.g., a small separation) by a lead structure that defines the pinhole collimators 74. Moreover, each detector array 70 may be formed from a plurality of CZT detector modules (e.g., two by two array), with each having a plurality of pixels (e.g., sixteen by sixteen pixels).

Accordingly, the displaced and angulated detector arrays 70 are configured for imaging a smaller or confined area, such as an organ of the patient, which may be performed faster than the general purpose imaging performed by the first and second general purpose gamma cameras 20 and 22. The detector arrays 70 may be formed and configured, for example, as a dedicated cardiac detector, such as an "Ultra-fast Cardiac" (UFC) detector array similar to the multi-pinhole cameras on the Discovery 530c imaging system available from GE Healthcare, which can image a heart in about three minutes.

In addition to the components described above in connection with the NM imaging system 10, other components may be provided. For example, in addition to the control and processing components for the organ specific gamma detector 30, a separate power supply and cooling system may be provided. As another example, an alphanumeric display 80 may be provided on a pivoting arm 82 mounted to the gantry 12. The alphanumeric display 80 in some embodiments is smaller than the display 56 and may provide the user with control or system operation information.

Figure 4:
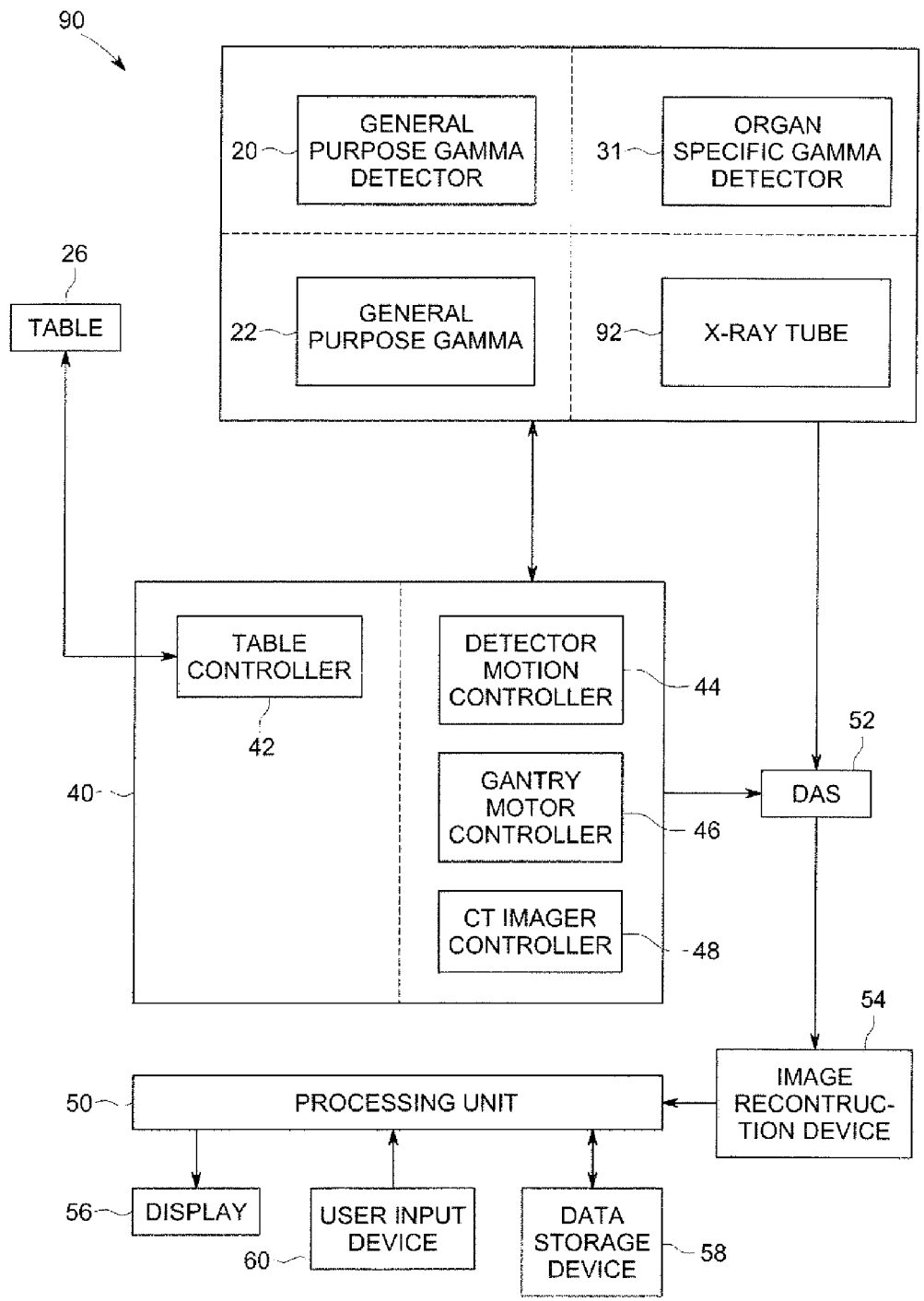
FIG. 4 is a block diagram of another imaging system formed in accordance with various embodiments.
Figure 5:
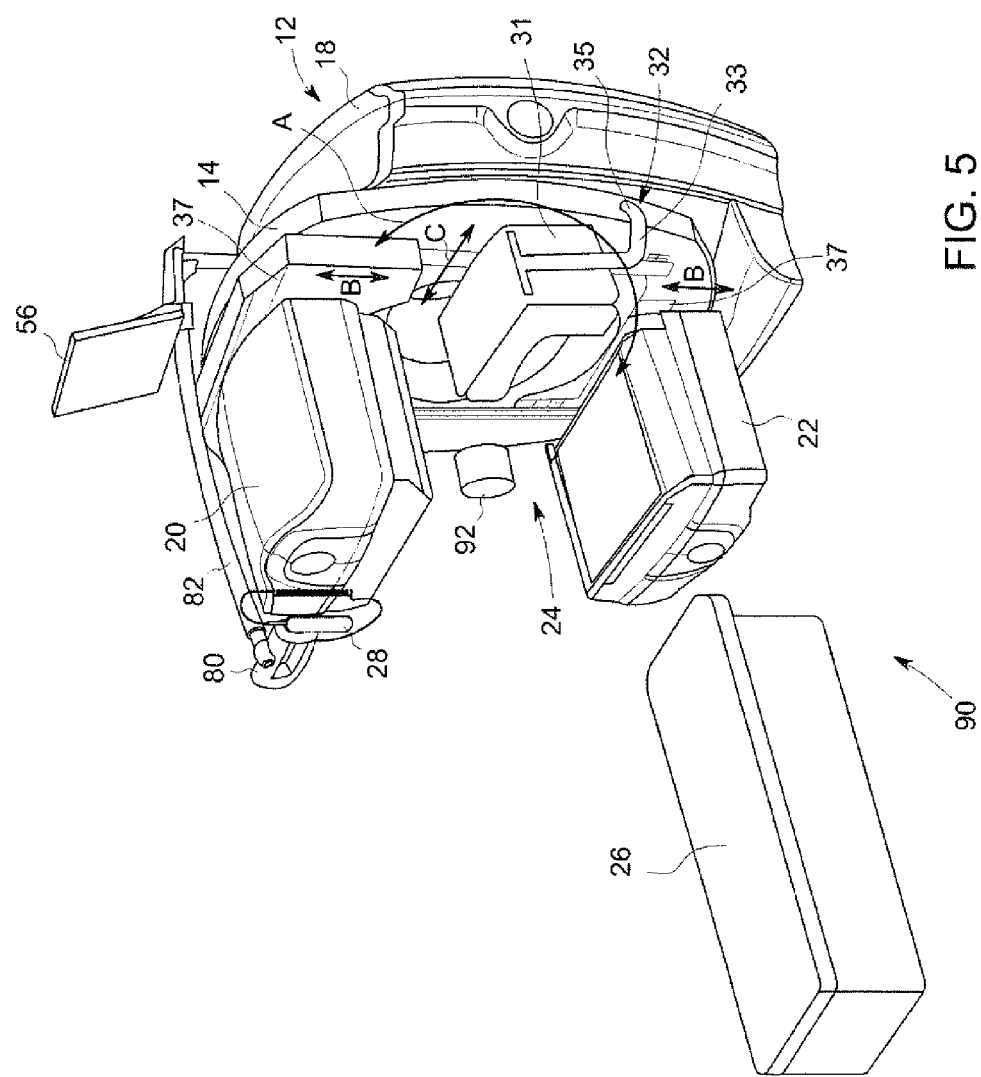
FIG. 5 is a perspective view of the imaging system of FIG. 4.

Other NM imaging system configurations also may be provided. For example, as shown in FIGS. 4 and 5, an NM imaging system 90 may be provided wherein like numerals represent like parts with the NM imaging system 10. The NM imaging system 90 also includes the first and second general purpose gamma cameras 20 and 22 provided on the first rotor 14. However, the second rotor 16 is not provided and an organ specific gamma detector 31 is instead mounted also to the first rotor 14 (and not the stator 18 as illustrated in FIGS. 1 and 2). Additionally, instead of the optional x-ray based CT imager 34, an x-ray source, and in particular, an x-ray tube 92 is optionally mounted to the first rotor 14. In particular, the x-ray tube 92 is mounted opposite the organ specific gamma detector 31 such that the x-ray tube 92 and the organ specific gamma detector 31 form an x-ray imaging system providing anatomical information and attenuation information similar to the CT imager 34 and as described in more detail below. In some embodiments, a slip ring (not shown) is provided between the first rotor 14 and the stator 18 to enable, for example, CT scanning.

In operation, the controller unit 40 uses the detector motion controller 44 in the same way as in the NM imaging system 10 to acquire NM imaging data using the NM imaging system 90. In addition to detecting nuclear emission for use in forming the images, the CZT detector modules of the organ specific gamma detector 31 also detect x-ray radiation from the x-ray tube 92 in the illustrated embodiment. For example, x-ray radiation may be detected in a current or counting mode of operation as is known, and optionally in a few energy windows. Thus, in the NM imaging system 90, the organ specific gamma detector 31 operates to perform both NM emission detection and CT imaging. The organ specific gamma detector 31 is connected to the first rotor 14 similar to the manner that the organ specific gamma detector 31 is connected to the stator 18 in the NM imaging system 10.

Accordingly, the organ specific gamma detector 31 can swivel or pivot out and away from the gantry 12, for example, when performing scanning using the first and second general purpose gamma cameras 20 and 22 or optionally may rotate with the rotor 14. The organ specific gamma detector 31 also is movable horizontally, namely toward and away from the examination axis 24 (as indicated by the arrow C), which may be performed manually by a user or in other embodiments optionally motorized and controlled by the detector motion controller 44. The organ specific gamma detector 31 is moved toward the examination axis 24 to be placed near the patient for NM organ imaging. Vertical motion and positioning of the patient is again provided using the patient table 26 controlled by the table controller 42.

Figure 6:
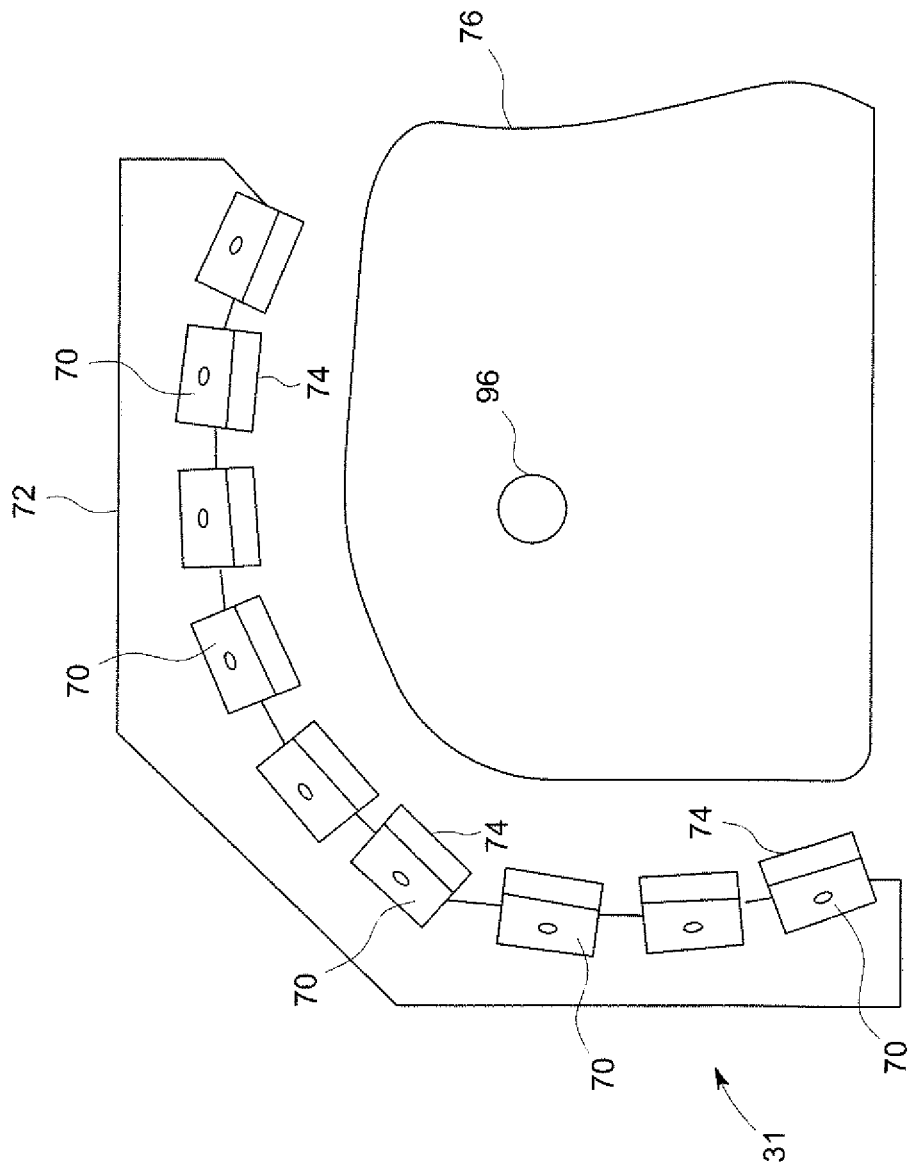
FIG. 6 is a diagram illustrating an organ specific gamma camera of the imaging system of FIG. 4 formed in accordance with various embodiments.

In the NM imaging system 90, the CZT detector modules of the organ specific gamma detector 31 are movable and aimable, for example, focused toward an organ of interest or toward the x-ray tube 92, for example, the x-ray focal point. In particular, the organ specific gamma detector 30 includes the plurality of solid-state two-dimensional (2D) detector arrays 70, for example, a plurality of Cadmium Zinc Telluride (CZT) detector arrays as shown in FIG. 6. Accordingly, the detector arrays 70 are focused gamma cameras for imaging a smaller region, such as an organ 96 of the patient 76 (e.g., heart, lung, brain, etc.). In the illustrated embodiment, the detector arrays 70 with the collimators 74 are focused to image a heart region within the patient 76. The detector arrays 70 also may be moved and focused on the x-ray tube 92, for example, to acquire x-ray information for anatomical registration and attenuation correction, which may occur as the first rotor 14 rotates to thereby acquire CT scan data. It should be noted that the collimators 74 in the NM imaging system 90 are not pinhole collimators.

The detector arrays 70 may be configured, for example, as described in co-pending U.S. application Ser. No. 11/498,630, entitled "Method and Apparatus for Imaging with Imaging Detectors Having Small Fields of View", which is commonly owned. Accordingly, the detector arrays 70 are independently movable. The detector arrays 70 may be arranged in different configurations, for example, in a close pack arrangement around a portion of the patient 76.

Figure 7:
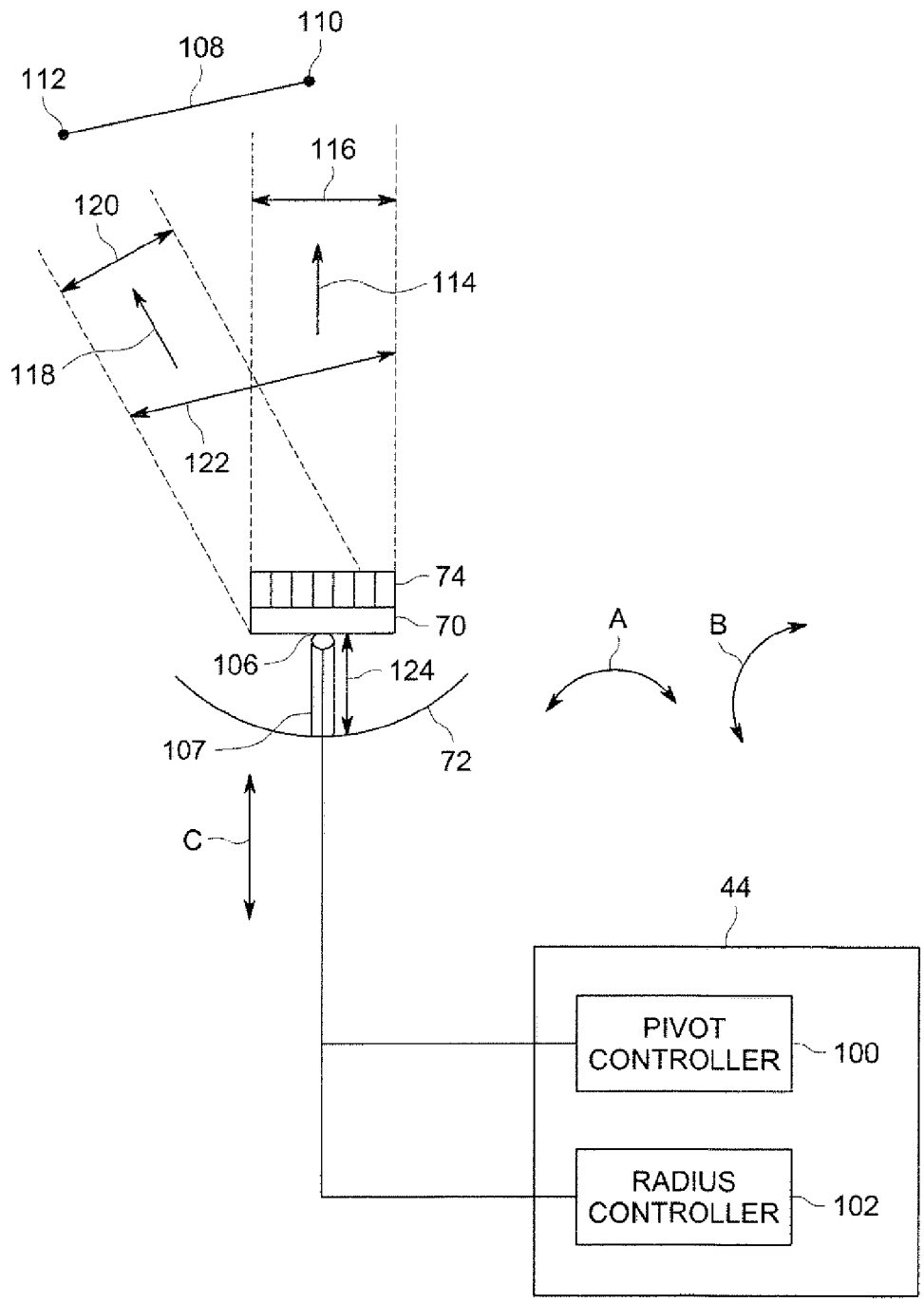
FIG. 7 is a diagram illustrating moving detector arrays of the organ specific gamma camera of FIG. 6 formed in accordance with various embodiments.
Figure 8:
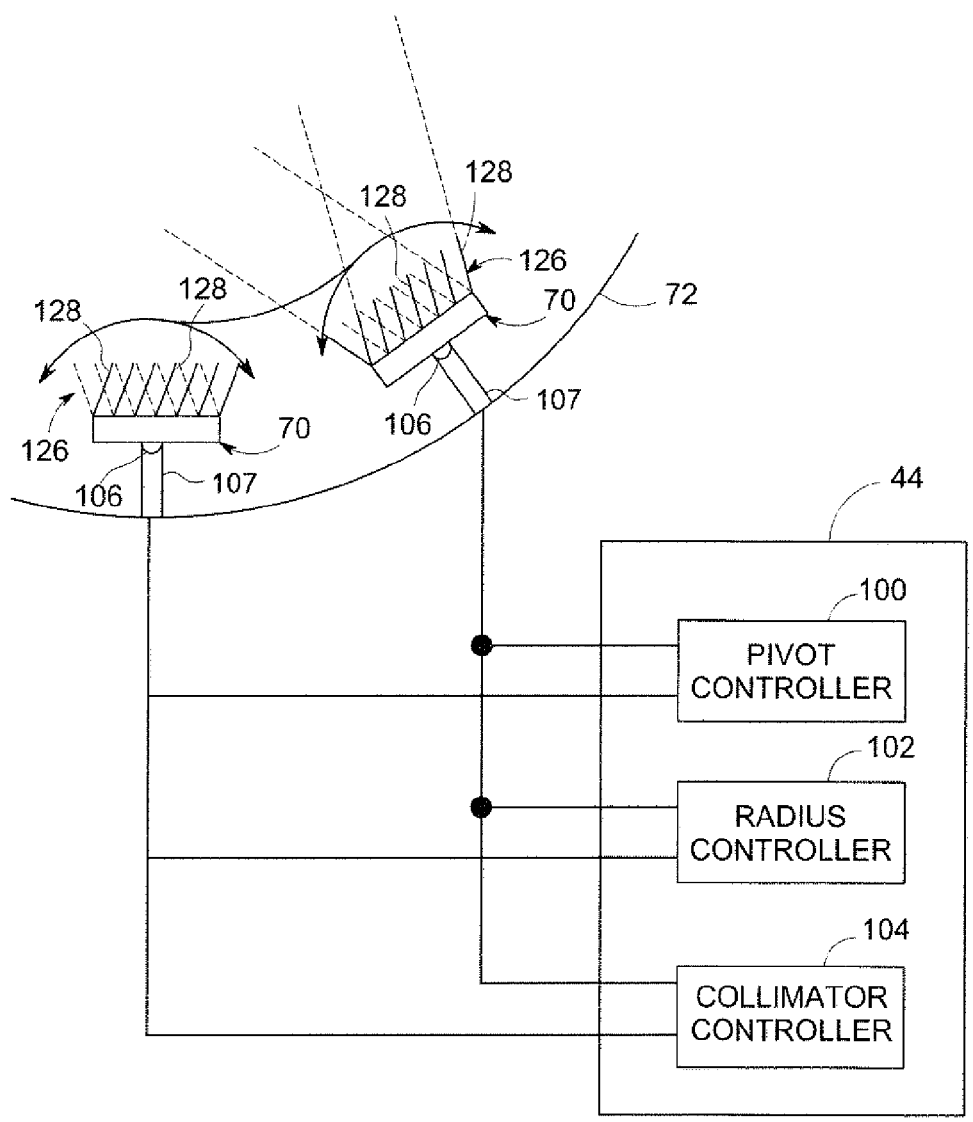
FIG. 8 is a diagram illustrating moving collimators of the organ specific gamma camera of FIG. 6 formed in accordance with various embodiments.

Thus, it should be noted that in various embodiments the configuration of the organ specific gamma detector 31 illustrated in FIG. 5 includes movable detector arrays and/or collimators, for example, as illustrated in FIGS. 6, 7 and 8. It also should be noted that in various embodiments when the CT imager 34 is provided, for example, as illustrated in FIG. 2, the configuration of the organ specific gamma detector 30 may be of the pinhole type as illustrated in FIG. 3 or the configuration of the organ specific gamma detector 31 may include movable detector arrays and/or collimators, for example, as illustrated in FIGS. 6, 7 and 8.

The detector arrays 70 each have a gamma emission and radiation detection face that may be directed towards a structure of interest within the patient 76 or towards the x-ray tube 92. In the various embodiments, the actual FOV for each of the detector arrays 70 may be increased, decreased, or relatively unchanged by the type of collimator, such as pinhole, parallel-beam converging, diverging fan-beam, converging or diverging cone-beam, multi-bore, multi-bore converging, multi-bore converging Fan-Beam, multi-bore converging Cone-Beam, multi-bore diverging, or other type of collimator.

In operation, the detector motion controller 44 in the NM imaging system 90 can also control the movement and orientation of the detector arrays 70 to keep the actual FOV of each of the detector arrays 70 directed towards or aimed at the structure or object of interest. The detector motion controller 44 in the NM imaging system 90 includes a pivot controller 100 and a radius controller 102 as shown in FIG. 7 illustrating control of a single one of the detector arrays 70. The detector motion controller 44 may move the detector arrays 70 individually, which may be in a fixed or predetermined relationship to one another. The pivot controller 100 may move each of the detector arrays 70 axially with respect to the patient 76 and the radius controller 102 may move each of the detector arrays 70 closer to and further from a surface of the patient 76. In some embodiments, for example, as illustrated in FIG. 8, a collimator controller 104 is provided as part of the detector motion controller 44 (or may be provided separately) and can adjust a position of an adjustable collimator, such as a collimator with adjustable strips (or vanes) or adjustable pinhole(s). It should be noted that motion of one or more of the detector arrays 70 may be in directions other than axially or radially, and optionally, motions in several motion directions may be combined to create the desired motion. Also, only a single type of motion, for example, pivoting motion may be provided. Therefore, the term "motion controller" may be used to indicate a collective name for all motion controllers.

In operation, prior to acquiring an image of the structure of interest or performing x-ray operations, the detector arrays 70, collimators 74, patient table 26 and/or first rotor 14 may be adjusted to focus a FOV on a structure or object of interest. Alternatively, one or more of the detector arrays 70 may not be used to acquire data if not needed. Thereafter, image data is acquired by each of the detector arrays 70, which may be combined and reconstructed into a composite image that may comprise 2D images, a 3D volume or a 3D volume over time (4D).

The detector arrays 70 may be moved such that, for example, an effective field of view for one or more of the detector arrays 70 may be reoriented or increased, such as by pivoting one or more of the detector arrays 70, translating one or more of the detector arrays 70 and/or adjusting one or more of the collimators 74. Referring specifically to FIG. 7, movement of one of the detector arrays 70 is illustrated, for example, to change the direction from which the respective detecting face of the detector array 70 senses gamma emissions or radiation. It should be noted that in this embodiment, the collimator 74 is illustrated as a parallel beam collimator 74. However, the collimator 74 may be other types of collimators as described herein.

The one or more detector arrays 70 may be mounted on a pivot 106 that is at the end of a support member 107 (e.g., a leg) mounted to the support structure 72 of the organ specific gamma detector 31. Other pivoting mechanisms may be used. The pivot controller 100 can command the pivot 106 to move along arrow A, along arrow B (which is orthogonal to arrow A), or any position between the arrows A and B. The pivoting motion may be used together with one or more of the other movements as described herein.

A pivot range 108 for each of the detector arrays 70 may be provided. For example, when imaging a structure that is larger than the actual FOV of the detector array 70 or to focus on a different object (e.g., change focus from a patient to an x-ray source), the pivot range 108 may have a start point 110 at one end wherein the FOV images one outer edge of the structure or is pointed toward a particular object. Optionally, a predefined amount of surrounding tissue may be imaged. An end point 112 of the pivot range 108 may be set to image an opposite outer edge of the structure as well as a predefined amount of surrounding tissue. Therefore, a pivot range 108 may be defined for each of the detector arrays 70 that may be specific to a particular scan.

Alternatively, one or more of the detector arrays 70 may be moved through a fixed, predetermined pivot range 108. A rate or speed of pivoting may also be predetermined, set by an operator, or determined based on the anatomy being scanned, size of the structure, level of radiation detected, and the like. It should be noted that rate of pivoting need not be constant throughout the pivot range 108, may be different for a different axis of pivoting, and may be different for different imaging detectors or throughout the duration of the acquisition. For example, the rate of pivoting may be higher during parts of the pivoting range 108 wherein the detector arrays 70 are aimed at the surrounding tissue. Thus, the detector arrays 70 collect more data from the structure of interest than from the surrounding tissue.

Moreover, the detector arrays 70 may remain focused on a particular area or may be adjusted or moved. For example, the detector arrays 70 may acquire image data at a first position 114 corresponding to the start point 110 of the pivot range 108. The actual FOV 116 of the detector array 70 is dependent in part upon the collimator 74. The detector array 70 is pivoted through the pivot range 108 along the direction of arrow A to a second position 118 corresponding to the end point 112 with an actual FOV 120. An effective FOV 122 that is larger than either of the actual FOVs 116 and 120 is formed. The detector arrays 70 may continuously acquire data while pivoting from the first position 114 to the second position 118. Alternatively, the detector arrays 70 may acquire a series of images as the pivot controller 100 moves the detector arrays 70 through the pivot range 108. Alternatively, the pivot controller 100 may move the detector arrays 70 to one or more predetermined positions within the pivot range 108, and the detector arrays 70 acquire images at each of the one or more positions. Although the example is illustrated in a single dimension, it should be understood that the effective field of view may be increased by pivoting the detector arrays 70 in other directions.

The support member 107 may be commanded by the radius controller 102 to move the detector arrays 70 toward and away from the patient 76 along arrow C. A distance 124 may thus be changed to increase or decrease the distance from the patient 76. The support member 107 may be piston driven, spring loaded, chain driven, or any other type of actuator. Alternatively, the support member 107 may be mounted on a segment (not shown) of the gantry, and thus the segment may also be driven in the direction of arrow C. The radius may be changed while acquiring data or between acquisitions, and may be used in combination with other motions. Anti-collision software and/or sensors (not shown) may also be used to ensure that the patient 76 does not collide with the detector arrays 70.

In some embodiments, adjustable collimators 126 are provided as shown in FIG. 8. As illustrated, the radius controller 102 may move each of the detector arrays 70 closer to and further from a surface of the patient 76, and the pivot controller 100 may move the detector arrays 70 axially with respect to the patient 76. Additionally, in this embodiment, the collimator controller 104 may adjust a position of the adjustable collimator 126, which may be a collimator with adjustable strips (or vanes) or adjustable pinhole(s). By changing the geometry of the adjustable collimators 126, the effective FOV may be changed or increased to be greater than the actual FOV. In a configuration wherein the collimators 126 include a plurality of strips 128, the collimator controller 104 can move all or a sub-set of the strips 128 through a range of motion. The collimator controller 104 may move the strips 128 predetermined distances, stop, and then acquire an image before moving the strips 128 to a next imaging position. Alternatively, the collimator controller 104 may move the strips 128 in a smooth sweeping motion, acquiring a single image across the effective FOV.

Thus, in the embodiment of FIG. 5, the configuration of the organ specific gamma detector 31 (as illustrated, for example, in FIGS. 6, 7 and 8) also operates as a CT detector as opposed to the configuration of the organ specific gamma detector 30 illustrated in FIG. 3 for the imaging system embodiment of FIG. 2. In the embodiments of FIGS. 5 through 8, the CZT modules of the organ specific gamma detector 31 are operated for both NM detection and CT detection. CT detection uses higher count rate (or "current mode" operation), however, in various embodiments the CZT detector is used in "count mode CT". In these embodiments, the "event detection threshold may be lowered to detect the lower energy x-ray. Also, due to the slow rotation of the first rotor 14 (NM detectors cannot rotate fast, as the detectors generally cannot withstand the "g forces" of fast rotation), the x-ray tube 92 is or operates at a lower power level. The CT acquisition takes longer, but this is compatible with the lower maximum x-ray flux that can be tolerated by the CZT (compared with "real CT" that uses scintillators plus photodiodes). The collimators of various embodiments are directed to point into or towards the x-ray tube 92. In multi-row (triplets) detector configurations, the outward rows of detector elements may be tilted in the "inward direction". This tilt may be permanent (which is also compatible with viewing the heart) or adjustable as described herein.

It should be noted that gaps may exist in the CT data set due to the gaps between the detectors. The gaps in the data may be overcome, for example, corrected or compensated for by iterative algorithms for the CT reconstruction. In various embodiments, the reconstruction of the NM data (both from embodiments of FIG. 2 or 5) is performed using one or more iterative algorithms, as the data set from the organ specific gamma detectors 30 and 31 is "incomplete" in the "classical" sense.

Thus, the various embodiments provide an NM imaging system that allows both large organ (e.g., whole body) imaging and fast small organ (e.g., heart) specific imaging. The NM imaging system of the various embodiments has a small footprint, is small in size and low cost. The NM imaging system of the various embodiments also allows for the acquisition of anatomical registration and attenuation correction information.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging system comprising:
   a gantry having a rotor and a stator;
   of pair of general purpose nuclear medicine (NM) gamma detectors configured to perform NM imaging of a region of interest, the general purpose NM gamma detectors coupled to the rotor;
   an organ specific NM gamma detector configured to perform NM imaging of a portion of the region of interest, the organ specific NM gamma detector pivotably and movably coupled to the stator such that the organ specific NM gamma detector can swing toward and away from the gantry in a sideways direction; and
   a mounting structure coupling the organ specific NM gamma detector to the stator and providing movable operation of the organ specific NM gamma detector to dispose the organ specific NM gamma detector between the pair of general purpose NM gamma detectors, wherein the mounting structure is configured to move the organ specific NM gamma detector to a first and second position, such that at the first position the organ specific NM gamma detector obstructs a rotation of the pair of general purpose NM gamma detectors and at a second position the rotation of the pair of general purpose NM gamma detectors is provided.

2. An imagine system in accordance with claim 1 wherein the mounting structure is configured to provide movement in a horizontal direction and configured to provide the pivoting movement of the organ specific NM gamma detector.

3. An imaging system in accordance with claim 1 wherein each detector of the pair of general purpose NM gamma detectors comprises a Sodium Iodide (NaI) based gamma camera and the organ specific NM gamma detector comprises a Cadmium Zinc Telluride (CZT) used gamma camera.

4. An imaging system in accordance with claim 1 further comprising a bracket and wherein the bracket movably couples the pair of general purpose NM gamma detectors to the rotor to allow movement in a single axis relative to the rotor.

5. An imaging system in accordance with claim 1 wherein the organ specific NM gamma detector comprises a plurality of solid-state detector modules each positioned in a fixed orientation.

6. An imaging system in accordance with claim 5 wherein the organ specific NM gamma detector comprises a plurality of pinhole collimators in front of the solid-state detector modules.

7. An imaging system in accordance with claim 1 wherein the organ specific NM gamma detector comprises a plurality of solid-state detector modules each movably positionable.

8. An imaging system accordance with claim 1 wherein the organ specific NM gamma detector comprises a dedicated focusing cardiac gamma camera.

9. The imaging system of claim 1, wherein the organ specific NM gamma detector further comprises detector arrays configured to conform to a shape of the patient such that each of the detectors in the array are displaced and angulated for imaging a confined area of the region of interest.

10. The imaging system of claim 1, wherein the pair of general purpose NM gamma detectors coupled to the rotor and the organ specific gamma detector are configured to provide NM imaging data that includes Single Photon Emission Computed Tomography (SPECT) information.

11. The imaging system of claim 1, wherein the pair of general purpose NM gamma detectors coupled to the rotor are configured to provide NM imaging data that includes Positron Emission Tomography (PET) information.

12. The imaging system of claim 1, wherein the pair of general purpose NM gamma detectors and the organ specific NM gamma detector are further configured to provide NM imaging data; the imaging system further comprising:
   a data acquisition system configured to receive the NM imaging data from the general purpose NM gamma detectors and the organ specific NM gamma detector, and to provide digital signals based on the NM imaging signal-data; and
   an image reconstruction device configured to receive the digital signals from the data acquisition system and to reconstruct an NM image using the digital signals.

13. A method of providing a nuclear medicine imaging system, the method comprising:
   coupling a pair of general purpose nuclear medicine (NM) gamma detectors to a rotor of a gantry; and
   using a mounting structure to pivotably and movably couple an organ specific NM gamma detector to a stator of the gantry such that the organ specific NM gamma detector can swing toward and away from the gantry in a sideways direction, the mounting structure configured to provide a movable operation of the organ specific NM gamma detector to dispose the organ specific NM gamma detector between the pair of general purpose NM gamma detectors, wherein the mounting structure is configured to move the organ specific NM gamma detector to a first and second position, such that at the first position the organ specific. NM gamma detector obstructs a rotation of the pair of general purpose NM gamma detectors and at a second position the rotation of the pair of general purpose NM gamma detectors is provided.

* * * * *